United States Patent [19]

Kress et al.

[11] B 3,985,759

[45] Oct. 12, 1976

[54] PROCESS FOR PREPARING 2-AMINO-5-CHLOROPYRIDINE

[75] Inventors: Thomas J. Kress, Indianapolis, Ind.; Larry L. Moore, Bargersville, Ind.

[73] Assignee: Eli Lilly and Company, Indianapolis, Ind.

[22] Filed: June 7, 1974

[21] Appl. No.: 477,252

[44] Published under the second Trial Voluntary Protest Program on January 13, 1976 as document No. B 477,252.

[52] U.S. Cl. ............................... 260/296 R; 71/92; 260/296 B; 260/296 H

[51] Int. Cl.² ...................................... C07D 213/02

[58] Field of Search ................................ 260/296 R

[56] References Cited
UNITED STATES PATENTS

| | | | |
|---|---|---|---|
| 3,579,528 | 5/1971 | Haszeldine et al. | 260/296 X |
| 3,849,429 | 11/1974 | Boudakian | 260/296 R |

OTHER PUBLICATIONS

Friedrich et al., Pharmazie, vol. 19, pp. 677 to 678, (1964).
Van Zweiten et al., Rec. Trav. Chim., vol. 80, pp. 1066 to 1074, (1961).
Klingsberg, Pyridine and its Derivatives, Part Two, frontis page and p. 308, (1961).
English et al., J. Am. Chem. Soc., vol. 68, pp. 453 to 458, (1946).

*Primary Examiner*—John D. Randolph
*Attorney, Agent, or Firm*—Mary Ann Tucker; Everet F. Smith

[57] ABSTRACT

2-Amino-5-chloropyridine is prepared by chlorinating 2-aminopyridine in a strongly acidic medium. 2-Amino-5-chloropyridine is a useful intermediate in the preparation of chloro-substituted-imidazo-pyridine herbicides.

5 Claims, No Drawings

PROCESS FOR PREPARING 2-AMINO-5-CHLOROPYRIDINE

BACKGROUND OF THE INVENTION

2-Amino-5-chloropyridine was first prepared by Tschischibabin [Chem. Zentr. 99II, 1670 (1928)] by chlorinating 2-aminopyridine in alcoholic solution. English et al, [J. Am. Chem. Soc., 68, 453 (1946)] and Van Zweiten et al., [Rec. Trav. Chim. 80, 1072 (1961)] prepared 2-amino-5-chloropyridine in 54 percent yield in 20 percent aqueous sulfuric acid at 25°C. Under such conditions significant amounts of 2-amino-3,5-dichloropyridine were produced as side products and low yields of the monochloro product were obtained.

2-Amino-5-chloropyridine also was prepared by reacting 2-aminopyridine with concentrated hydrochloric acid in the presence of an oxidizing agent. [Pharmazie, 19 (10), 677 (1964)]. Yields of the monochloro product of about 70 percent were obtained by this process with relatively slight formation of other chlorination products.

It was not recognized previously that selective monochlorination and higher yields of product are obtained by efficient protonation of the 2-aminopyridine reactant in a strongly acidic medium and chlorination of the selectively reactive protonated species.

Thus, it is an object of this invention to provide a process for preparing 2-amino-5-chloropyridine with only minimal concomitant production of the dichloro over-chlorination product.

It is a further object of this invention to provide a process for preparing 2-amino-5-chloropyridine in greater yield than previously has been accomplished.

SUMMARY OF THE INVENTION

The present invention relates to a novel process for preparing 2-amino-5-chloropyridine which comprises reacting 2-aminopyridine with a chlorinating agent in a strongly acidic medium having a Hammett acidity function of less than −3.5. In such a strongly acidic medium, the selective monochlorination of 2-aminopyridine to provide 2-amino-5-chloropyridine is accomplished with minimal contamination from the 2-amino-3, 5-dichloropyridine over-chlorination by-product.

2-Amino-5-chloropyridine may be nitrated to give the corresponding 3-nitropyridine compound, followed by acylation to yield 5-chloro-3-nitro-2-fluoroacylamidopyridine, and reduction to provide 6-chloro-1-hydroxy-2-fluoroalkyl-1-H-imidazo-(4,5-b)-pyridine compounds which are useful as herbicides as disclosed in Belgian Pat. No. 764591.

DETAILED DESCRIPTION OF THE INVENTION

It has been discovered that reacting 2-aminopyridine with a chlorinating agent in a strongly acidic medium having a Hammett acidity function, $H_o$, of less than about −3.5 results in the production of 2-amino-5-chloropyridine with only minimal formation of the 2-amino-3,5-dichloropyridine overchlorination by-product.

While there is no wish to be bound to any theory of reaction mechanism, it is believed that in such a strongly acidic medium having an acidity function of less than −3.5, the chlorination process of the invention takes place through the formation of a reactive protonated species of 2-aminopyridine which thereafter undergoes selective mono-chlorination according to the following generalized reaction scheme.

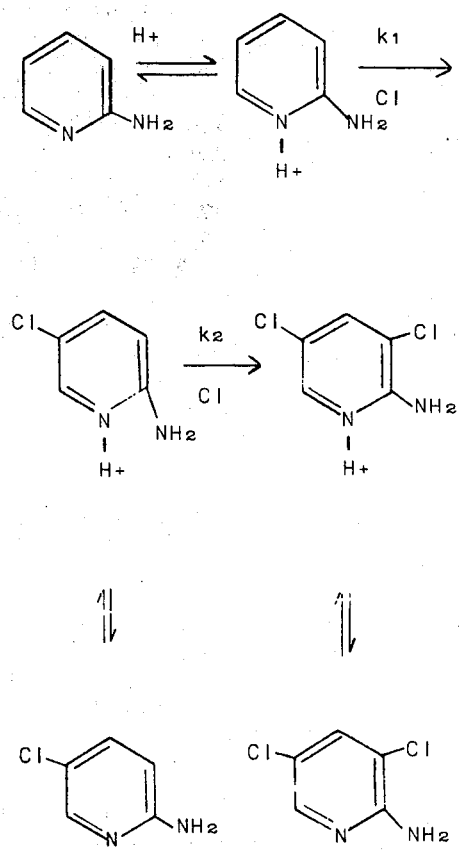

In the above reaction scheme, the rate of chlorination of protonated 2-aminopyridine, $k_1$, is much greater than the rate of chlorination of protonated 2-amino-5-chloropyridine, $k_2$. Thus, the selective monochlorination reaction predominates in strongly acidic medium and competitive over-chlorination reactions are minimized.

In a weakly acidic medium, e.g. 20% sulfuric acid, however, the 2-aminopyridine reactants are present largely in unprotonated form. The rates of chlorination of unprotonated 2-aminopyridine and unprotonated 2-amino-5-chloropyridine are comparable. Therefore, the subsequent over-chlorination reaction resulting in the formation of substantial amounts of 2-amino-3,5-dichloropyridine is competitive with the desired monochlorination reaction.

The presence of over-chlorination products in the reaction mixture makes recovery of the desired pure 2-amino-5-chloropyridine product difficult. In addition, the further chlorination of 2-amino-5-chloropyridine to form 2-amino-3,5-dichloropyridine reduces the yield of the desired product.

Conveniently, the 2-aminopyridine starting material is added to the strongly acidic medium with external cooling to maintain the reaction mixture at about room temperature during the addition. At least one equivalent of a chlorinating agent is then added to the reaction mixture with stirring. The use of less than one equivalent of the chlorinating agent results in incomplete chlorination of starting material and consequently reduces the yield of the desired product. Preferably, between about one and about two equivalents of the chlorinating agent per equivalent of 2-aminopyridine starting material are employed. More than two equivalents of the chlorinating agent may be employed, but the use of a large excess of chlorinating agent tends to increase the formation of over-chlorination by-products without further promoting the desired complete reaction of the starting material.

Slow addition of the chlorinating agent to the reaction mixture is preferred. Most preferably, the chlorinating agent is added at about the rate at which it is consumed. Such slow addition prevents the buildup of large excesses of chlorinating agent in the reaction mixture and thus minimizes the production of over-chlorination by-products. While the temperature of the reaction mixture may be controlled if desired, external control of the reaction mixture temperature during addition of the chlorinating agent is not necessary.

After addition of the chlorinating agent is completed, the reaction mixture is stirred at ambient temperature for about 30 minutes to about 90 minutes. Longer reaction times are conducive to the formation of 2-amino-3,5-dichloropyridine and preferably are avoided.

The reaction mixture, containing 2-amino-5-chloropyridine as the hydrochloride salt, is poured onto ice with stirring and made basic (pH greater than 7) to precipitate 2-amino-5-chloropyridine. The product is recovered using conventional techniques.

The strongly acidic medium necessary to the process of the invention comprises any strong acid/polar unreactive solvent system which is sufficiently acidic to effect substantially complete protonation of 2-aminopyridine and 2-amino-5-chloropyridine. The acidity of a medium, that is, the activity and concentration of hydrogen ion, typically is determined via pH measurements. Such measurements, however, have accurate meaning only in very dilute solutions in a single solvent, usually water. In concentrated solutions or in nonaqueous or mixed solvent systems some other parameter is necessary to measure the acidity of the solution. Thus, an acidity function is a measure of the proton donating ability of a medium and is important in kinetic investigations of acid catalyzed reactions.

The best known and most widely used such function is the Hammett acidity function, $H_o$. This function is very useful for comparing acidities of different media and is far superior to simple stoichiometric acid concentrations. The Hammett acidity function is defined as follows:

$$H_o = pK_a + \log\left[\frac{C_B}{C_{BH^+}}\right]$$

wherein $C_B/C_{BH^+}$ is the ratio of the concentration of the indicator present in the medium as a neutral base to the concentration present as the conjugate acid.

The above equation furnishes a method for the experimental determination of the acidity function value, $H_o$. All that is necessary is to add to a medium an indicator (usually a weak aniline base) for which the value of pKa is known and to measure the indicator ratio $C_B/C_{BH^+}$ colorimetrically. Values of $H_o$ for various acidic media can be plotted against the percent composition and such tabulations are available. [See C. H. Rochester, *Acidity Functions*, Academic Press, London and New York (1970); O'Conner, *J. Am Chem Soc.*, 46, 686 (1969); Paul et al., Chem Rev., 57, 1 (1957)].

In order to effect substantially complete protonation of 2-aminopyridine and 2-amino-5-chloropyridine, it is necessary to employ a strongly acidic medium having a Hammett acidity function less than about −3.5, and preferably less than −4.5. As the value of $H_o$ for the medium decreases, the protonation of the pyridine reactants in that medium becomes more complete and the formation of dichloro by-products is suppressed. If the acidic medium has an acidity function greater than about −3.5, a substantial amount of unprotonated species is available for chlorination with the consequent formation of significant amounts of over-chlorination by-products.

Strong acids which may be used in the process of the invention include sulfuric acid, perchloric acid, hydrochloric acid, and the like. Nitric acid is not suitable for use in this process, both because it is not sufficiently acidic and because competing nitration of the pyridine ring takes place in nitric acid solutions.

Suitable polar unreactive solvents include water, formic acid, acetic acid, aromatic solvents such as nitrobenzene, and the like.

Representative of the strongly acidic media useful in the process of the present invention are aqueous sulfuric acid having a sulfuric acid content of at least 60 percent by weight, aqueous perchloric acid having a perchloric acid content of at least 60 percent by weight, hydrogen chloride-glacial acetic acid having a hydrogen chloride content of at least 10 percent by weight, sulfuric acid-glacial acetic acid having a sulfuric acid content of at least 30 percent by weight, and like mixtures of a strong acid and a polar unreactive solvent having an acidity function less than −3.5.

Concentrated aqueous hydrochloric acid (37 percent by weight) also can be employed in the process of the invention. This medium is not preferred, however, since it has an acidity near the minimum level effective to efficiently protonate completely the pyridine reactants.

When the strongly acidic medium has an acidity function only slightly less than −3.5, only one equivalent of the chlorinating agent preferably is employed, since the use of an excess of the chlorinating agent results in the production of undesirable amounts of over-chlorination by-products. 2-amino-5-chloropyridine of satisfactory purity is obtained by using one equivalent of the chlorinating agent and a medium having an acidity function only slightly less than −3.5, for example 37 percent aqueous hydrochloric acid. The yield of product, however, is somewhat less than that which is obtained by employing an excess of the chlorinating agent, up to about two equivalents, and a medium having an acidity function less than −4.5.

Preferred media are 70 percent aqueous sulfuric acid or 10 percent by weight hydrogen chloride in anhydrous acetic acid; most preferred is 70 percent aqueous sulfuric acid.

One of the aspects of using a polar unreactive solvent other than water, for example acetic acid, in the strongly acidic medium is the relatively high acidity given the strong acid in an anhydrous polar solvent as compared with aqueous solutions. Thus, a medium composed of hydrogen chloride and glacial acetic acid may be used effectively in the selective mono-chlorination process of the invention, although an aqueous hydrochloric acid medium is not entirely satisfactory, as discussed above.

The addition of water to a solution of a strong acid and a nonaqueous polar solvent results in a substantial decrease in the acidity of the solution. Therefore, a medium in which the strong acid is hydrochloric acid preferably is prepared by adding an appropriate amount of hydrogen chloride gas to the polar solvent under essentially anhydrous conditions.

Any of the commonly used chlorinating agents which are well known in the art and are stable in strongly acidic medium, for example chlorine gas, hypochlorous acid, thionyl chloride, sulfuryl chloride and the like, may be employed in the process of the invention. The choice of a chlorinating agent depends somewhat on the polar solvent which is employed, however, since the chlorinating agent must be unreactive with the solvent of choice.

The chlorinating agent may be added to the reaction mixture either in pure form or mixed with a suitable diluent or solvent which is miscible with the reaction medium. Preferably, such diluent or solvent is the same strongly acidic medium which is used as the reaction medium, since dilution of the acidic reaction medium with a diluent or solvent of lesser acidity is detrimental to the process of the reaction.

Solid chlorinating agents preferably are dissolved in the same mixture of a strong acid and a polar solvent which is used as the acidic reaction medium, and are added to the reaction mixture dropwise.

Liquid or gaseous chlorinating agents preferably are not mixed with a diluent or solvent and are added dropwise and bubbled into the reaction mixture respectively.

The preferred chlorinating agent is chlorine gas, because any unreacted chlorine is easily removed from the reaction mixture at room temperature by venting the reaction vessel at the completion of the reaction. Preferably the chlorine gas is condensed using a dry-ice condenser until an appropriate amount for use in the reaction is obtained. The chlorine then is allowed to evaporate slowly and is added to the reaction mixture through a gas addition tube. In this manner both the quantity of the chlorinating agent and the rate of addition of the chlorinating agent to the reaction mixture are easily controlled.

The starting material used in the process of the invention, 2-aminopyridine, is a known compound which is commercially available. The ratio of the molar concentration of 2-aminopyridine to the molar concentration of acid used in the strongly acidic medium preferably is no greater than 1 to 5, since higher ratios of the basic starting material tends to reduce the acidity of the reaction mixture below an effective level.

The following examples are provided to further illustrate this invention. It is not intended that this invention be limited thereby, either in spirit or in scope, since it is apparent to those skilled in the art that many modifications both of materials and methods may be practiced within the purpose and intent of this disclosure.

EXAMPLE 1

To a 250 ml. round bottom flask equipped with a paddle stirrer, gas addition tube, thermometer, and dry-ice condenser, was added 94 ml. of 72.4 percent by weight aqueous sulfuric acid. 2-Aminopyridine (18.8 g., 0.20 mole) was added to the sulfuric acid in 3–4 g. portions with external cooling to maintain the temperature of the solution at about 25°C. Chlorine gas was condensed in a dry-ice condenser until 17.2 ml (28.4 g., 0.40 mole) of liquid chlorine was obtained. Chlorine gas obtained from evaporation of the liquid chlorine was added beneath the surface of the reaction mixture over a two-hour period. The temperature of the reaction mixture dropped slowly to −20°C. and, after completion of the chlorine addition, the solution was stirred for an additional 1.5 hours with chlorine reflux. At the end of this period, the condenser was removed, the solution was allowed to come to room temperature, and the excess chlorine was vented. The solution then was poured into ice and water and the pH was adjusted to pH 10 with 25 percent aqueous sodium hydroxide. The resulting slurry was filtered and the light tan solid was washed with cold water. After drying two hours in vacuo at 50°C., the yield of 2-amino-5-chloropyridine was 22.3 g. (86.8 percent, 98.7% purity as determined by vapor phase chromatographic analysis) m.p. 137°–137.5°C.

EXAMPLE 2

Eighty-five ml. of concentrated aqueous hydrochloric acid (37 percent by weight) was added to a flask equipped similarly to that in Example 1. 2-Aminopyridine (18.8 g., 0.20 mole) was added to the hydrochloric acid in small portions with external cooling to maintain the temperature of the solution at about 25°C. Chlorine gas (9.5 ml, 14.9 g., 0.21 mole) was condensed as in Example 1 and added to the reaction mixture over a period of one hour. The temperature of the reaction mixture rose to 53°C during addition of the chlorine. The solution was stirred for an additional hour with very slight chlorine reflux, after which the condenser was removed and the excess chlorine was vented. The solution then was poured onto ice and made basic with 50 percent aqueous sodium hydroxide. The resulting precipitate was collected by filtration and washed with cold water. The filtrate was extracted 3 times with chloroform and the combined extracts were washed with water and dried over sodium sulfate. The drying agent was filtered off and the filtrate evaporated to dryness. The combined yield of 2-amino-5-chloropyridine was 17.8 g. (69.4 percent, 96.4% purity).

EXAMPLE 3

2-Aminopyridine (18.8 g., 0.20 mole) was dissolved in 100 ml. glacial acetic acid in a flask equipped similarly to that in Example 1. Hydrogen chloride gas was bubbled into the solution until 10.5 g. had been added. Chlorine (11.5 ml, 17.7 g., 0.25 mole) was condensed as in Example 1 and added to the reaction mixture over a period of 45 minutes. The temperature of the reaction mixture was maintained at about 10°C. to about 12°C. during the chlorine addition by means of an ice bath. The reaction mixture was stirred for an additional 30 minutes with very slight chlorine reflux. The condenser then was removed and the excess chlorine was vented. The solution was poured over ice and made basic with 50 percent aqueous sodium hydroxide. The resulting precipitate was collected by filtration, washed with cold water and dried in vacuo. 19.6 g. of 2-amino-5-chloropyridine was obtained (76.3 percent yield, 92.8% purity).

we claim:

1. A process for preparing 2-amino-5-chloropyridine which comprises reacting 2-aminopyridine with no more than two equivalents of a chlorinating agent selected from the group consisting of chlorine gas, hypochlorous acid, thionyl chloride, and sulfuryl chloride in a strongly acidic medium having a Hammett acidity function less than −3.5.

2. The process of claim 1 wherein the strongly acidic medium has a Hammett acidity function less than −4.5.

3. The process of claim 2 wherein the chlorination reaction is carried out in an aqueous sulfuric acid medium containing at least 70 percent by weight sulfuric acid.

4. The process of claim 1 wherein the chlorination reaction is carried out in a hydrogen chloride-glacial acetic acid medium containing at least 10 percent by weight hydrogen chloride.

5. The process of claim 1 wherein said chlorinating agent is chlorine gas.

* * * * *